United States Patent [19]

Morrow

[11] Patent Number: 5,674,537
[45] Date of Patent: Oct. 7, 1997

[54] ELECTROLYZED SALINE SOLUTION CONTAINING CONCENTRATED AMOUNTS OF OZONE AND CHLORINE SPECIES

[75] Inventor: Robert E. Morrow, Salt Lake City, Utah

[73] Assignee: Medical Discoveries, Inc., Layton, Utah

[21] Appl. No.: 477,293

[22] Filed: Jun. 7, 1995

Related U.S. Application Data

[60] Division of Ser. No. 275,904, Jul. 15, 1994, Pat. No. 5,622,848, which is a continuation-in-part of Ser. No. 527,321, May 23, 1990, Pat. No. 5,334,383.

[51] Int. Cl.$^6$ .................... A61K 38/44; A61K 35/00; A61K 33/40; A01N 1/02
[52] U.S. Cl. .................... 424/613; 424/94.4; 424/123; 424/661; 435/2; 435/243
[58] Field of Search .................... 424/94.4, 123, 424/613, 661; 435/2, 243

[56] References Cited

U.S. PATENT DOCUMENTS

| | | | |
|---|---|---|---|
| 3,282,823 | 11/1966 | Richards | 204/272 |
| 3,443,055 | 5/1969 | Gwynn et al. | 219/83 |
| 3,479,275 | 11/1969 | Gwynn et al. | 204/275 |
| 3,616,355 | 10/1971 | Themy et al. | 204/149 |
| 4,201,651 | 5/1980 | Themy | 204/217 |
| 4,236,992 | 12/1980 | Themy | 204/278 |
| 4,316,787 | 2/1982 | Themy | 204/242 |
| 4,968,616 | 11/1990 | Inoue et al. | 435/188 |
| 4,970,216 | 11/1990 | Deckner et al. | 514/311 |
| 4,976,959 | 12/1990 | Berger, Jr. et al. | 424/94.2 |
| 5,028,588 | 7/1991 | Hoffman et al. | 514/6 |

FOREIGN PATENT DOCUMENTS

| | | |
|---|---|---|
| 55-87712 | 7/1980 | Japan . |
| 56-32422 | 4/1981 | Japan . |
| 1-259001 | 10/1989 | Japan . |

OTHER PUBLICATIONS

"Simple, Safe and Economical Way to Disinfect Municipal Drinking Water", Brinecell, Inc. Mar. 1992.

*Primary Examiner*—John W. Rollins
*Assistant Examiner*—Deborah K. Ware
*Attorney, Agent, or Firm*—Thorpe, North & Western, L.L.P.

[57] ABSTRACT

A microbiocidal solution for in vivo and in vitro treatment of microbial infections containing an electrolyzed saline solution having a content of regulated amounts of ozone and active chlorine species. The ozone content is 5 to 100 mg/L (milligram per liter) and the chlorine species content is 5 to 300 parts per million (ppm). The active chlorine species comprises free chlorine, hypochlorous acid and the hypochlorite ion as measured by a chlorine selective electrode. The solution is prepared by subjecting a 1% or less saline to electrolysis under conditions sufficient to produce the active ingredients. The solution is used at an isotonic saline concentration and my be adjusted with hypertonic saline. The solution is used in vitro treatments of infected whole blood, blood cells or plasma to reduce contamination. The solution may also be administered to warm blooded animals, including humans by intravenous injection.

6 Claims, No Drawings

ELECTROLYZED SALINE SOLUTION CONTAINING CONCENTRATED AMOUNTS OF OZONE AND CHLORINE SPECIES

This application is a divisional of application Ser. No. 08/275,904 filed Jul. 15, 1994, now U.S. Pat. No. 5,622,848 which is a continuation-in-part of patent application Ser. No. 07/527,321 filed May 23, 1990, now U.S. Pat. No. 5,334,383.

This application relates to the in vitro and in vivo antimicrobial use of electrically hydrolyzed salines. More particularly, this invention relates to the in vitro treatment of pathogen contaminated fluids and the in vivo treatment of microbial (including viral) infections or conditions in warm blooded animals.

The use of ozone ($O_3$) for the treatment of viral infections has been documented for over thirty years. Typical publications illustrating antiviral activity include Wehrli, *Transactions of the VI Congress of the European Society of Haematology*, 1:318 (1957); Wolff, vjm Heidelberg 2. Auflage (1982); Rilling, vjm Heidelberg, 2 Auflage (1986); Mattasi et al., *Medical Applications of Ozone*, ed. LaRaus J. Norwalk, International Ozone Association, pp. 134-137 (1985); Konrad, *Medical Applications of Ozone*, ed. LaRaus J. Norwalk, International Ozone Association, pp. 140-146 (1985) and Jacobs, *Ozonachrichten*, 1-5 (1986). Stephens, et al, *Science*, 231:589-594 (1986) reports the use of ozone in the treatment of equine infectious anemia, a viral infection analogous to HIV in horses.

Chlorine, in the form of chlorinated lime was used successfully as early as 1846 by Semmelweiss to prevent and fight puerperal fever. By 1911 the United States purified as much as 800,000,000 gallons of water through the chlorination process. Wide use of chlorine as a 0.05% sodium hypochlorite solution (Dakins Solution) for open and infected wounds began in 1915. Dakins Solution was a standard product up to 1963 listed in the British Pharmacopeia.

Both ozone and chlorine have demonstrated in vitro anti-HIV activity as shown by Carpendale, *Antiviral Research*, 16:281-292, (1991) and Martin et al., *J. Infect. Dis.*, 152:400-403 (1985).

As reported by Wilk et al., *International Congress on Technology and Technology Exchange*, First Euro-American Symposium, Paris, France (1992) and *Science, Total Environment*, 63:191-197 (1987), certain combinations of ozone and chlorine have significantly greater activity than either used separately against a variety of bacteria including *Staphylococcus aureus* and *Pseudomonas aeruginosa*. *Candida albicans* was also reported to be effectively killed by a combination of ozone and chlorine.

In warm-blooded animals, there is a natural defense mechanism which produces in vivo naturally occurring free radicals in order to respond to antigens or other infectious pathogens.

Phagocytic cells (neutrophils, monocytes, eosinophils, macrophages), and large granular lymphocytes (collectively called "killer cells") give off superoxide in what is called the "respiratory burst," which has an antimicrobial action and, if not properly controlled, can also cause tissue damage. The superoxide radical itself may not be directly responsible for the microbicidal action. Rather, this activity and any resultant tissue damage may be attributed to superoxide derivatives such as hydrogen peroxide, hydroxyl radical and possibly, singlet oxygen. Polymorphonuclear neutrophils and macrophages not only give off superoxide, leading to the production of hydrogen peroxide and hydroxyl free radicals, but also generate hypohalous acids and N-chloroamines as one of their mechanisms which also destroy bacteria. These leukocytes consume oxygen, which is transformed by membranous reduced nicotinamide adenine dinucleotide phosphate (NADPH) oxidase to superoxide.

The "respiratory burst" is observed as a dramatic increase in the consumption of oxygen and the activation of a membrane-associated NADPH oxidase. This oxidase reduces molecular oxygen to superoxide anions, which in turn dismutates to hydrogen peroxide. Superoxide and hydrogen peroxide can interact to give rise to the hydroxyl radical and possibly also to singlet oxygen. The superoxide anion, hydrogen peroxide, hydroxide radicals and singlet oxygen, all possess antimicrobial activity and are quiteunstable. The respiratory burst continues during phagocytosis by polymorphonuclear leukocytes until engulfment is complete. The respiratory burst may also occur in leukocytes under various chemical influences in addition to phagocytosis.

The respiratory burst, although intimately connected with phagocytosis, is not an essential accompaniment to phagocytosis. Recent evidence suggests that free tissue macrophages and newly recruited monocytes, as distinguished from fixed tissue macrophages, can respond to lymphokines and phagocytic stimuli by mounting a respiratory burst. The failure of fixed tissue macrophages, such as Kupffer cells, to produce active metabolites of oxygen may be important in protecting tissues from damage during the scavenger functions of the macrophage. Many soluble agents, including antigen/antibody complexes, C5a, ionophores and tumor promoters, can trigger the respiratory burst without phagocytosis. The respiratory burst can also be triggered by opsonized particles or surfaces when phagocytosis is frustrated by the use of a drug such as cytochalasin B. In addition to the reactive species of oxygen referred to above, i. e. superoxide anions, hydrogen peroxide, hydroxyl radicals, and singlet oxygen, there are a number of other potential microbicidal mechanisms in macrophages, many of which are oxygen dependent. A major oxygen dependent system is mediated by myeloperoxidase (MPO), which catalyzes oxidation of a number of substances to hydrogen peroxide. MPO is the oxidase of neutrophils, and the green color of pus is due to its presence. A cofactor in the MPO system is the iodide ion from the thyroid hormones, thyroxine or triiodothyronine. However, this microbicidal system sometimes also utilizes other halide ions such as bromide or chloride as cofactors in the place of iodide.

It is well documented that two free radicals of superoxide combine with hydrogen to form normal oxygen and hydrogen peroxide. This is known as the dismutation reaction with superoxide dismutase (SOD) acting as the catalyst. Unless hydrogen peroxide is denatured promptly, with catalases or peroxidases, there is an interaction between superoxide and hydrogen peroxide leading to the production of the highly reactive hydroxyl radicals via pathways known as the Haber-Weiss or Fenton's reactions. Singlet oxygen is also generated by the removal of the unpaired electrons of the superoxide radical.

Leukocytes, in vivo, use the formation of superoxide, hydrogen peroxide, hydroxide radicals, singlet oxygen and halogenated products such as hypochlorous acid to destroy bacteria, fungi and viruses and perhaps also tumor cells. Other oxygen-dependent antimicrobial systems, unrelated to MPO, are also believed to rely on the production of hydrogen peroxide, superoxide anion, the hydroxyl radical and/or singlet oxygen to do the microbial killing in vivo. Some of these systems are not well documented but it is known that when such systems shut down or operate inefficiently, severe infections results.

There may be problems involved with over production or an excess of these radicals within the cells of the host. Hence, the body has provided means for mediating or neutralizing these products once they have performed their antimicrobial functions.

As previously mentioned SOD is effective in scavenging superoxide radicals (each containing an unpaired electron) in a simultaneous oxidation-reduction reaction with hydrogen called dismutation. Two superoxide radicals combine with two hydrogen atoms to form hydrogen peroxide and oxygen. Hydrogen peroxide is reduced by the enzymes catalase, glutathione peroxidase and MPO into oxygen and water.

Hence, in a normal functioning host, such as in a human or other warm blooded animal, there is an intra vivo interaction and balance maintained between respiratory bursts brought on by the presence of an invading foreign substance such as bacteria, virus or fungi accompanied by the formation of superoxide, hydrogen peroxide, hydroxyl radicals, singlet oxygen, hypohalous acids, and hypochlorite ions [collectively referred to as free radicals] with their accompanying antimicrobial actions and the mediating or neutralizing action of the enzymes SOD, MPO, glutathione, glutathione peroxidase, catalase, ascorbic acid and its salts and perhaps others.

There are situations, both in vivo and in vitro, when there are not sufficient free radicals present to accomplish their desired antimicrobial tasks. There are numerous bacterial, viral and fungal related syndromes and immunological disorders wherein it would be beneficial to have free radicals such as ozone and active chlorine species available to cells and/or fluids for the short period required for their antimicrobial action followed, if necessary, by mediation and/or neutralization of the free radicals. Examples of such syndromes and/or immunological disorders for which either in vitro or in vivo treatment could be beneficial are Epstein-Bart virus, hepatitis A, B and C, rhinovirus, rubeola, rubella, parvovirus, papilloma virus, influenza and parainfluenza viruses, enteroviruses; Herpes simplex viruses; Varicellazoster viruses, Adenoviruses, respiratory syncytial viruses, alphaviruses, flaviviruses, retroviruses (including AIDS and AIDS related syndromes), bacteremia, septicemia, fungal infections, parasitic infections (nematodes, trematodes, protozoal [e.g., Cryptosporidium] helminthic), mycobacterial infections, bacterial Gram positive and Gram negative superficial and systemic infections and other viral, bacterial and/or fungal associated diseases. Many of these are diseases which are affected by a slow, latent or temperate organism, (i.e. virus, bacterium or fungus) which may have long incubation periods and, in some cases, have a low ratio of reported cases to infections. Many of these are also diseases for which there is no known cure and usually slowly progress until they, or a concurrent opportunistic infection, results in the death of the host.

An infected host or patient may be treated by a variety of regimens which may alleviate the symptoms for a time. However, the immune system eventually is weakened to the point that it can no longer adequately contend with the invading or autoimmune related infections and the natural biocidal action in the cells ceases to function properly.

There are also situations where fluids can be beneficially treated in vitro, to purify, decontaminate, or otherwise render such fluid acceptable for administration to a warm-blooded host. For example, the blood supply taken from donors at blood banks has been found on occasion to be contaminated by the HIV virus and other organisms such as hepatitis A, B and C viruses, CMV (cytomegalovirus), and bacteria (such as Yersinia). Any treatment of whole blood, plasma or cell isolates to render them benign from infectious organisms without destroying the therapeutic characteristics of such fluids would be very beneficial.

In pending patent application Ser. No. 07/527,321 it is shown that an electrolyzed saline solution, properly made and administered in vivo, is effective in the treatment of various infections brought on by invading antigens and particularly vital infections resulting in cardiomyopathy, multiple sclerosis and AIDS. In that application, a restriction requirement was issued such that the issued claims in that application are drawn to the treatment of cardiomyopathy and multiple sclerosis. The present invention is directed to embodiments not the subject of the claims allowed in the original application and data developed in support thereof.

OBJECTS AND SUMMARY OF THE INVENTION

It is an object of the present invention to provide a method of treating microbe related infections wherein an electrolyzed saline solution containing regulated amounts of ozone and active chlorine species is injected into the body of a warm blooded animal which mimics or enhances the naturally occurring free radicals produced by respiratory bursts in the cells in responding to such infections.

It is also an object of this invention to provide a method of treating microbe related infections by injecting an electrolyzed saline solution containing regulated amounts of ozone and active chlorine species into the bloodstream of a warm blooded animal along with the administration of moderating or neutralizing agents which enables the body to utilize such chemicals as microbiocides in the same manner as it does during in vivo respiratory bursts.

A still further object of this invention is to provide a method of treating antigenic related infections by the coadministration of electrolyzed saline solutions containing free radicals and colchicine into the bloodstream of a warm blooded animal along with the administration of moderating agents to enhance the ability of the body to utilize the free radicals as microbiocides.

Yet another object of this invention is to provide a method of treating microbial infections by the administration of a precisely regulated electrolyzed saline.

A yet different object of this invention is to provide a method for the in vitro decontamination or treatment of microbially contaminated solution by an electrolyzed saline containing amounts of ozone and active chlorine species.

Another object of this invention is to provide an electrolyzed saline containing regulated amounts of ozone and active chlorine species in concentrations sufficient to bring about the desired disinfection, antimicrobial or decontamination properties when utilized for the desired in vitro or in vivo purposes.

These and other objects may be accomplished by means of first preparing a dilute saline solution, subjecting this solution to electrical hydrolysis with adequate voltage, amperage and time to produce an electrolyzed solution containing ozone and active chlorine species in designated concentrations and also containing other products of the electrolysis reaction including members elected from the group consisting of hydrogen, sodium and hydroxide ions. The interaction of the electrolysis products results in a solution containing bioactive atoms, radicals or ions selected from the group consisting of chlorine, ozone, hydroxide, hypochlorous acid, hypochlorite, peroxide, oxygen and perhaps others along with corresponding amounts of molecular hydrogen and sodium and hydrogen ions. Preferably the finished solution will have an ozone concentration of about 5 to 100 mg/liter and an active chlorine species concentration of between about 5 and 300 ppm. By active chlorine species is meant the total chlorine concentration attributable to chlorine content detectable by a chlorine ion selective electrode and will be selected from the group consisting of chlorine, hypochlorous acid and hypochlorite ions or moieties. The pH of the solution is preferably between about 7.2 and 7.6 and, when used for intravenous administration, most preferably between about 7.35 and 7.45 which is the pH range of human blood. Preferably the ozone content will be between about 5 to 30 mg/L and the active chlorine species content will be between about 10 and 100 ppm. Most preferably, the ozone content will be between about 9 to 15 mg/L and the active chlorine species content will be between about 10 and 80 ppm.

The injecting of effective amounts of the regulated electrolyzed solution intravenously into a warm blooded animal affected by an infectious agent results in a microbicidal action which mimics or enhances action of the free radicals produced in vivo as a result of respiratory bursts.

If necessary, the regulated electrolyzed saline solution may be injected along with the administration of moderating and/or neutralizing amounts of antioxidants or reducing agents such as catalase, superoxide dismutase, MPO or other suitable peroxidase, glutathione, glutathione peroxidase, ascorbic acid or other suitable agents. The moderating antioxidants and/or neutralizing agents may be administered just prior to, concurrent with or shortly following the administration of the electrolyzed saline solution. Also, the antioxidants or neutralizing agents may be administered either orally, intravenously or parenterally. Additionally, the microbicidal effects of the electrolyzed solution may be enhanced by the coadministration of effective amounts of colchicine and perhaps other enhancing agents. However, it is not always necessary, or even desirable, to administer moderating agents due to the fact that the active ingredients of the electrolyzed saline dissipate rapidly into innocuous products and the dosage administered is sufficiently regulated to prevent unwarranted side effects and/or damage to tissues in the host.

When used for the in vitro treatment of fluids for antimicrobial purposes the active agents are neutralized or converted into inert products in a time frame without harmful exposure to cellular or organ systems, alleviating the need for the use of neutralizing agents. Fluids that can be beneficially subjected to such in vitro treatment include blood, blood cells, blood plasma, and mixtures thereof.

DETAILED DESCRIPTION OF THE INVENTION

The products resulting from the electrolysis of saline solutions has long been known as has the fact that such solutions are in vitro microbicides for hard surfaces. Themy, U.S. Pat. Nos. 4,236,992 and 4,316,787 are drawn to a novel electrode, method and apparatus for electrolyzing dilute saline solutions to produce effective amounts of disinfecting agents such as chlorine, ozone and hydroxide ions. One apparatus for producing electrolyzed saline solutions was previously available under the tradename Ster-O-Lizer. Laboratory reports and other data available from testing of electrolyzed saline solutions from various Ster-O-Lizer models have shown that it is effective in keeping water free of pathogenic organisms. Tests conducted in vitro further show that certain microorganisms, inclusive of *Pseudomonas aeruginosa*, *Escherichia coli*, *Staphlococcus aureus*, *Candida albicans*, and *Salmonella typhi*, are non-infectious after exposure to electrolyzed saline solutions. However, it has not heretofore been shown that physiological fluids treated by electrolyzed saline containing finite amounts of ozone and active chlorine species to destroy microbes is safe for administration to warm blooded animals.

Although it is known that electrolyzed saline solutions possess in vitro microbicidal activity it has long been thought that components in the electrolyzed solution, such as ozone and chlorine, are toxic to warm blooded animals and should not be utilized for in vivo purposes. It has now been found, however, that saline solutions, which have been subjected to electrolysis to produce finite amounts of ozone and active chlorine products, can be injected into the vascular system to create a reaction to assist in the removal, passivation or destruction of a toxin. When desired, to mimic or enhance the physiological action in immunological/cellular "respiratory bursts" to the generated microbicide, one or more of several modulating chemicals may be added to the complete treatment. These modulating chemicals are administered before, concurrent with or after the electrolyzed saline and may be administered intravenously, parenterally or, in some cases, orally.

In copending application Ser. No. 07/527,321 filed May 23, 1990, now U.S. Pat. No. 5,334,383, it was considered that 100–300 ppm of chloride was the desired component along with other reaction products of the electrolysis. At the time that application was filed the inventor did not have in his possession such equipment as could accurately determine ozone or active chlorine species content. The term "chloride" as used in that application meant the active chlorine content of the solution and not the chloride ion per se. The use of superior electrodes for the electrolysis reaction and more sensitive detection or analytical equipment has shown that the electrolyzed solutions can have an ozone content which can vary between about 5 to 100 mg/liter and an active chlorine species concentration of between about 5 and 300 ppm. The pH of the solution is preferably between about 7.2 and 7.6 and, when used for intravenous administration, most preferably between about 7.35 and 7.45, which is the normal pH range of blood. Preferably the ozone content will be between about 5 to 30 mg/L and the active chlorine species content will be between about 10 and 100 ppm. Most preferably, the ozone content will be between about 9 to 15 mg/L and the active chlorine species will be present in amounts ranging between about 10 and 80 ppm. While the chloride content as stated in the copending application is within the ranges considered as operative, if it had been accurately been measured by a chlorine selective electrode, it would most likely have been lower and comparable with the solution exemplified in Example I which follows.

When the electrolyzed saline is injected into the vascular system of a warm-blooded animal the active agents are transported rapidly throughout the system and pass intracellularly into cells affected by invading microorganisms. The components of the solution pass readily through cell walls and function in the manner described above for free radicals. Chlorine is thought to be present primarily as free chlorine or as a hypochlorite ion. However, the primary microbicidal action of chlorine and its compounds comes through the formation of hypochlorous acid. This acid is formed upon the combining of free chlorine and water. Hypochlorites undergo hydrolysis with the formation of hypochlorous acid.

The hypochlorous acid then decomposes to form hydrochloric acid and nascent oxygen. Nascent oxygen is a strong oxidizing agent having microbicidal action. Chlorine also interacts directly with intracellular substances as a microbicide. The hypochlorite ion is also microbicidal. Sodium hypochlorite has long been used as an antiseptic, disinfectant and sterilant. It has found use in dilute form, about 0.5% concentration, in surgery and in dissolving and deodorizing necrotic tissue. It has also been used to irrigate ragged or dirty wounds and as an antiseptic in certain peritoneal dialysis systems.

For purposes oft his invention, the term active chlorine agent or species, shall mean any active form of chlorine resulting from the subjecting of a saline solution to electrolysis which can be measured by a chlorine selective electrode. These species will be primarily free chlorine, hypochlorous acid and the hypochlorite ion.

The intracellular actions of the hydroxide ion have previously been described.

In certain situations where it may be desired to utilize higher concentrations of chlorine and oxygen active agents produced from the electrolysis of a saline solution to accomplish their microbiocidal purposes, it may be desirable to concurrently administer in vivo or subject a solution in vitro to modulating or moderating chemicals. As used herein the terms "moderating", "modulating" and "neutralizing" agents may be used interchangeably.

The modulating chemicals are enzymes or reducing agents which interact with and reduce the active microbicidal agents to innocuous compounds. The enzymes are inclusive of, but not limited to, the superoxide dismutases (SOD), catalase and glutathione peroxidase. As previously stated, they function to remove the superoxides, peroxides and hydroxides that are formed in the cells. Otherwise oxygen toxicity results. These oxygen radicals are converted to hydrogen peroxide by Cu/Zn activated superoxide dismutases (SOD) in the cells. In a properly functioning system the hydrogen peroxide is then converted to oxygen and water by a catalase. If the hydrogen peroxide and the superoxide radical are allowed to combine, the more deadly hydroxide radical is formed.

The primary activated SOD in warm-blooded animals is Cu, Zn-superoxide dismutase. This metalloenzyme undergoes a reduction-oxidation cycle with the superoxide radical with the net result of dismutation of the superoxide radical to hydrogen peroxide and oxygen. The metals required for this activity are copper and zinc. Other forms, i. e. Mn-SOD and Fe-SOD, are also known but occur primarily in bacteria and cellular mitochondria. Without the presence of copper, the SOD enzyme is virtually inactive in the animal. The activity of the Cu, Zn-SOD enzyme can be suppressed by the too rapid accumulation of hydrogen peroxide. Therefore, it is essential that other enzymes which deplete hydrogen peroxide be functional within the cell to maintain SOD activity.

Catalase is a large molecular weight enzyme that contains four heme groups per molecule. Catalase is the primary enzyme necessary for the breakdown of hydrogen peroxide in the cell to oxygen and water and is found in all cells of the body that utilize oxygen.

Glutathione peroxidase (GSH-Px) has a selenium dependent form which contains four moles of selenium per mole of the enzyme. The oxidative role of this enzyme is similar to catalase in that it converts hydrogen peroxide to water and oxygen. Whenever catalase or glutathione peroxidase activity is impaired there can be a toxic build-up of peroxides. This, in turn, can lead to a build-up of the hydroxide radical. The non-selenium glutathione peroxidase (GSH-P) plays a role in controlling lipid peroxidation. The primary form of glutathione peroxidase within the red blood cell is the selenium dependent form.

Glutathione and ascorbic acid are both reducing agents involved in biological systems of oxidation.

Glutathione is a tripeptide of cysteine, glutamic acid and glycine. It is most often isolated from animal tissues in the form of its cuprous salt. The oxidized form is readily reduced by tissues to the sulfhydryl form. The latter form, in the presence of traces of copper gives up its hydrogen to molecular oxygen, becoming oxidized in turn. In other Words, in the oxidized form it acts in the cells as a hydrogen acceptor and in the reduced form, as a hydrogen donor. The oxidized form is reduced by glutathione reductase. Glutathione appears to be a ubiquitous reducing agent involved in many intracellular redox reactions.

Ascorbic acid (Vitamin C) functions in a number of biochemical reactions, mostly involving oxidation. It is a reducing agent associated with the regeneration and maintenance of the connective tissue. Vitamin C has been shown to be an effective stimulator to the immune system. As a strong reducing agent it is used as an antioxidant to neutralize the oxidizing chemicals in the electrolyzed saline solution. Ascorbic acid is also a coenzyme for the oxidation of glutathione. Ascorbic acid is readily absorbed from the intestine. It is present in the plasma and is ubiquitously distributed in the cells of the body. Hence, it may be orally administered. However, intramuscular or intravenous injections of either ascorbic acid or sodium or calcium ascorbate may also be utilized when faster action is preferred.

Timely administration of one or more of these modulating agents prevents the toxic effects where and when excess amounts of oxidizing agents are present following administration of the electrolyzed saline solution.

The sterile saline solution that is to be subjected to treatment in the electrolysis unit has an initial concentration of about 0.25 to 1.0% NaCl which is about one-fourth to full strength of normal or isotonic saline solution. According to Taber's Cyclopedic Medical Dictionary, E. A. Davis, Co. 1985 Ed., an "isotonic saline" is defined as a 0.16M NaCl solution or one containing approximately 0.95% NaCl; a "physiological salt solution" is defined as a sterile solution containing 0.85% NaCl and is considered isotonic to body fluids and a "normal saline solution" a 0.9% NaCl solution which is considered isotonic to the body. Therefore, for purposes of this disclosure, the term "isotonic", "normal saline", "balanced saline" or "physiological fluid" is considered to be a saline solution containing between about 0.85 and 0.95% NaCl. The saline solution may be subjected to electrolysis at concentrations between about 0.15 and 1.0%. Preferably the solution will be diluted with sterile distilled water to the desired concentration, preferably between about 0.15 to 0.35%, and subjected to electrolysis at sufficient voltage, amperage and time to produce an electrolyzed solution. The electrolysis reaction is carried out at ambient temperatures in a sterile atmosphere. Obviously, the voltage and amperage to be used and the time of electrolysis is subject to many variables, i.e. the size and composition of the electrodes, the volume and/or concentration of saline being electrolyzed. For large electrodes or saline volumes or higher concentrations of saline solutions the voltage, amperage or time may be higher and/or longer. It is the generation of the desired concentration of ozone and active chlorine species which is important. According to Faraday's laws of electrolysis, the amount of chemical change produced by a current is proportional to the quantity of electricity passed. Also, the amounts of different substances liberated by a given quantity of electricity are proportional to the chemical equivalent weights of those substances. Therefore, to generate an electrolyzed saline having the desired concentrations of ozone and active chlorine species from saline solutions having a saline concentration of less than about 1.0%, voltage, amperage and time parameters appropriate to the electrodes and solution are required to produce an electrolyzed solution containing between about 5 to 100 mg/L of ozone and a free chlorine content of between about 5 to 300 ppm. For in vitro use these solutions can be utilized without further modification or they can be adjusted as desired with saline or other solutions. Prior to in vivo use, this solution may be adjusted or balanced to an isotonic saline concentration with sufficient hypertonic saline, e.g. 5% hypertonic saline solution.

Generally speaking, such microbiocidal solutions will have an ozone content of between about 5 and 100 mg/L and an active chlorine species content of between about 5 and 300 ppm. Preferably the ozone content will be between about 5 to 30 mg/L and the active chlorine species content will be between about 10 and 100 ppm. Most preferably the ozone content will range between about 9 to 15 mg/L and the active species content will be between about 10 and 80 ppm. An effective amount of this balanced microbiocidal saline solution is then administered by appropriate modes, e.g. intravenously, orally, vaginally or rectally and may vary greatly according to the mode of administration, condition being treated, the size of the warm-blooded animal, etc. For human beings to be injected intravenously the dosage of this balanced electrolyzed solution may vary from between about 0.25 to 4 ml/kg/day body weight with ranges of 0.5 to 3.0 ml/kg/day being preferred. The doses can be divided into smaller doses and administered two or more times per day or may be administered in a single dose. Also, the regimen may vary according to the indication being treated. For HIV treatments, for example, it may be advantageous to administer the microbiocidal solution for several days followed by a rest period and then repeating the cycle for as long as necessary or as indicated by the test results, e.g. of Western Blot, T cell subsets, chem profile (SMAC 20), CBC, p24 antigen and HIV mRNA quantitation. A typical regimen might be five days of treatment followed by two days rest and the cycle repeated for two months. Depending on clinical status or laboratory tests, this regimen may be reduced to, e.g. three days of treatment per week for six weeks. These regimens are exemplary only and are not meant to be limiting as any number or variation might be dictated according to circumstances.

When utilized, the amount of moderating agent to be administered will depend somewhat upon the method and time of administration. Dosages of moderating agents administered orally will be somewhat higher than if injected intravenously. Also, if the modulating agent is administered before injection of the electrolyzed saline, there must be sufficient time allowed for the modulating agent to be absorbed and carried into the bloodstream to the site where it can reduce the remaining free radicals from the electrolyzed saline after the solution has accomplished its microbicidal function.

The dosage of modulating agent or agents to administer is not necessarily stoichiometric with the free radicals of the electrolyzed saline and may initially have to be determined empirically. There should be sufficient modulating agent in the system to prevent the free radical components of the electrolyzed saline from causing irreparable tissue damage. For that reason, it may be beneficial to administer modulating agents such as the superoxide dismutase, catalase, L-glutathione, glutathione peroxidase, MPO and ascorbic acid orally for a period of time prior to the injection of the electrolyzed saline to provide the availability of adequate amounts of these agents in the cells at the time the electrolyzed saline is injected. However, it is equally important that the free radical components be available to perform their desired microbicidal function before being suppressed or deactivated by the modulating agents. As a generalization only, oral dosages of superoxide dismutase varying from about 5,000 to 60,000 units per day may be administered. Catalase, MPO and glutathione peroxidase dosages may vary between about 10,000 to 120,000 units per day. Glutathione may be administered in amounts ranging from about 10 to 120 mg per day. Ascorbic acid or its sodium or calcium salts may be administered over a wide range of about 50 to 20,000 mg per day. Preferably, the ascorbic acid is administered intravenously shortly after the injection of the electrolyzed saline to make sure that no unreacted oxidative components of the saline are reduced and/or neutralized. Based on the above guidelines, one skilled in the art can readily determine what is an effective amount of modulating agent.

By injecting the electrolyzed saline intravenously and administering the modulating agent in the manner described above, there is created in the cells the same elements as are created naturally in the body to fight infections. In other words, the electrolyzed saline solution mimics the action of the free radicals produced during the respiratory burst from the macrophages and monocytes. Similarly, the modulating agents mimic the action of the enzymes produced by macrophages and monocytes as reducing agents to neutralize the oxidants. This results in a straight forward attack on the microorganisms within the host cell by the injected chemicals.

The coadministration of colchicine with the electrolyzed saline may also prove beneficial as an adjunct in preventing replication of the invading microorganisms. Colchicine, [N-(5,6,7,9-Tetrahydro-1,2,3,10-tetramethoxy-9-oxobenzo[a]heptalen-7-yl_)acetamide] $C_{22}H_{25}NO_6$, is a major alkaloid of *Colchicum autumnale*. It is an anti-inflammatory agent used primarily as a gout suppressant and in the treatment of Familial Mediterranean Fever, scleroderma and psoriasis. It functions by inhibiting the migration of granulocytes into an inflamed area, reducing the release of lactic acid and proinflammatory enzymes that occur during phagocytosis, thereby breaking the cycle that lead to the inflammatory response. The neutrophils and leukocytes produce glycoproteins which bind cells and may be a cause of acute inflammation. Colchicine prevents either the production by or release from leukocytes of glycoproteins. It also produces a temporary leukopenia that is soon replaced by a leukocytosis, sometimes due to a striking increase in the number of basophilic granulocytes and may have the same action in increasing lymphocyte production. The site of action is apparently directly on the bone marrow. Moreover, colchicine is an antipyretic, lowering body temperature. It also increases the sensitivity of the body to CNS depressants, depresses the respiratory center, enhances the response to sypathomimetic agents, constricts blood vessels and induces hypertension by central vasomotor stimulation. It is well tolerated in moderate dosage and, although not a corticosteroid, acts much like cortisone in suppressing the immune system without the attendant high risk and side effects of corticosteroids. In low dosages, colchicine may work as an immune system stimulant helping to relieve an overworked immunosystem.

While not known for a certainty, it is believed that colchicine functions in the present invention primarily in preventing the release of glycoproteins which bind cells and breaks the cycle of inflammatory response. Other secondary effects may be that it functions as an antimitotic, antiviral agent, as a mild immunosuppressant and produces a leukocytosis by stimulating the bone marrow.

To understand why the use of colchicine to prevent the release of glycoproteins may be an important adjunct to the present invention, the following information regarding HIV and AIDS is beneficial. This extreme vital infection is popularly referred to as AIDS (acquired immune deficiency syndrome). However, it is more appropriately an HIV (human immunodeficiency virus) infection leading to AIDS. This disease proceeds through various stages from HIV exposure to HIV infection to development of AIDS. These stages are classified by Redfield, et al. in an article entitled "The Walter Reed Staging Classification for HTLV-III/LAV Infection" published in the New England Journal of Medicine, Volume 314, Page 131, January, 1986, and are referred to as the Walter Reed (WR) classification. They are thus referred to as WR0 through WR6. The WR0 classification means there has been exposure to the HIV virus although there are no symptomatic indications. WR1 means there is a positive HIV antibody and/or virus determination but no other symptoms. A WR2 classification is characterized by chronic lymphadenopathy or swollen lymph nodes in addition to positive HIV antibody and/or virus determination. A WR3 classification is reached when the T4-cell count drops and remains below 400 cells per cubic millimeter of blood. The normal T4-cell count is about 800. There may or may not be chronic lymphadenopathy in WR3 through WR6 classifications but the T4-cell count stays below 400. A patient moves to the WR4 stage after partial sub-clinical (asymptomatic) defects are found in delayed hypersensitivity, i.e. the ability to react to skin tests that are a barometer of immune functioning. The line into WR5 is crossed when the patient completely fails to respond to the skin test or when thrush (a fungal disease of the mouth) develops. Lymphadenopathy and abnormalities of the T4-cell and skin tests must persist for at least three months to serve as valid criteria. Patients enter into the WR6 stage and are said to have AIDS when opportunistic infections, which occur because the immune system has broken down, develop elsewhere in the body. Typical opportunistic infections include Kaposi's sarcoma, cryptococcal meningitis, cytomegalovirus (causing blindness) and classic *Pneumocystis carinii* pneumonia.

The HIV virus is a retrovirus which does not per se cause death of its host. However, the presence of the HIV virus contributes to the decline of T4-cells in the body. The T4 lymphocytes, or T4-cells, recognize foreign antigens or infected cells. Upon recognition, the T4-cells help activate another set of white blood cells called B-lymphocytes. These B-cells then multiply and produce specific antibodies that bind to the infected cells and other organisms containing the antigen. The binding of the antibodies to the antigen containing cells or organisms inactivates and/or destroys those cells or organisms.

The T4-cells have other functions as well. They orchestrate cell-mediated and humoral immunity by killing infected cells or infecting microbes with antibodies and cytotoxic cells such as T8 lymphocytes and white cells known as killer cells. The T4-cells also influence mobile scavenger cells known as monocytes and macrocytes. These scavengers engulf infected cells and foreign particles and secrete a variety of cytokines. The cytokines are small but highly potent proteins that modulate the activity of many cell types, including T and B cells. The T4-cells also secrete cytokines on their own which stimulate the proliferation of T and B cells in the body.

From the above, it is apparent that the loss of T4-cells can seriously impair the body's ability to fight microbe-caused diseases and vital infections in particular. The eradication of these invading microbes requires a highly-orchestrated cell-mediated response. Without T4-cells this immune response does not function satisfactorily.

According to Redfield et al., "HIV Infection: The Clinical Picture," *Scientific American,* 259:90, October, 1988, there is a balance of power between the HIV virus and the immune system arranged by the T4-cells. From the WR0 (exposure stage) to the WR1 stage the HIV virus increases rapidly at which point the immune system begins to respond. By the time the WR2 stage is reached the viable virus in the body has dropped dramatically with the concomitant rise in scavengers, macrophages, T-cells, B-cells, antibodies and other immune system components. The immune system remains somewhat in control throughout the WR2 and into the WR3 stages although there is a gradual rise in HIV. However, by the time the WR4 stage is reached the HIV has begun to overwhelm the immune system and the T4-cells become so depleted that the balance of power switches, and, from that point on, the HIV replicates wildly, overwhelming the remaining T4-cells and any vestiges of immune defense.

How the HIV virus infects and kills T4 cells raises many questions leading to certain theories and/or conclusions. Infection begins as a protein, gp120, on the viral envelope binds tightly to a protein known as the CD4 receptor on the cell surface. The virus then merges with the T4 cell and reverse transcribes its RNA genome into double-strand DNA. The viral DNA becomes incorporated into the genetic material in the nucleus of the cell and directs the production of new vital RNA and viral proteins which combine to form new virus particles. These particles bud from the cell membrane and infect other cells.

Under certain circumstances the HIV virus can multiply prodigiously in the helper T cells and kill them, suggesting that viral replication is the main cause of cell destruction. In particular, it has been found that HIV replication and cell deaths increase when infected helper T cells become activated, as they do when they take part in an immune response to other infections. Thus, the very immunological process that should defeat the HIV virus has the opposite effect of increasing the proliferation of the virus.

Further investigation reveals an apparent paradox, i.e. HIV replication could be demonstrated in only a small fraction of T4 cells collected from HIV infected patients. The cells killed by replication alone might hamper the immune system somewhat, but that would not cause the severe immune deficiency seen in AIDS. However, another mechanism for T4 cell destruction, one which is compatible with the present invention, may be explained by the formation of syncytia or massive bodies consisting of many merged cells having multinuclei. Syncytia develops after a single cell becomes infected with HIV and produces vital proteins, including gp120, which is displayed on the surface of the infected cell. Because gp120 and the CD4 receptors of the T4 cells have a high affinity for each other, uninfected T4 cells can agglomerate and/or bind to the infected cell and merge with it. The resulting syncytium cannot function and dies. The original infected cell is killed, but so are myriad uninfected T4 cells that could otherwise be used to attack and kill the HIV vies.

Furthermore, in a process that is unique to the HIV infection, free viral gp120 protein may circulate in the blood and the lymph system and bind to the CD4 receptors of uninfected helper T cells, making them susceptible to attack by the immune system. Regardless of how helper T cells are killed by HIV, the decline in number of cells leads to a more general decline in immune functioning leading through the six stages of the disease progression referred to above.

It is believed that colchicine blocks the release of glycoproteins, i.e. gp120, which promote adhesion between the cells as described above. In the development of syncytia, the T4 cells are bound together to create megacells of infected and uninfected leukocytes which cannot carry out their immune function. It is believed that the colchicine dissolves and/or prevents the glycoprotein bond. This action prevents the T4 cells from agglomerating and releases the uninfected leukocytes (T-cells) to be active in an immune response and prevents their death and eventual depletion.

There is also believed to be a synergistic effect in that the liberation of infected T4 cells from the glycoprotein also renders them more available, and hence susceptible, to the microbicidal action of the free radical type components of the electrolyzed saline solution. Moreover, colchicine is a mild immunostimulant which may slow the replication of the virus lying dormant inside T4 cells. This dormant virus is waiting for an outside infection to stimulate an immune response which will activate viral replication.

When used, the dosage of colchicine may vary between about 1.0 to 3.0 mg, with about 1.5 mg being considered optimal for adults. It is preferably administered intravenously just prior to or concurrent with the administration of the electrolyzed saline solution.

As noted above, colchicine is used as an adjunct to the administration of the electrolyzed saline. The most advantageous treatment of any disease is the use of the minimal amount of any active agent needed to accomplish the desired results. In many instances the use of colchicine may not be indicated or even desired.

If desired in order to conclude the treatment, about 500 to 5000 mgs, and preferably about 1000 to 4000 mgs of ascorbic acid, or its sodium or calcium salt, is administered about two to twenty minutes after the injection of the electrolyzed saline. This reducing agent neutralizes the remaining unreacted active components of the electrolyzed saline.

While moderating agents and/or colchicine may supplement the administration of electrolyzed saline containing quantitated amounts of ozone and active chlorine species, it is the quantitated saline and its uses to which this invention is particularly drawn. Therefore, the administration of moderating agents and/or colchicine are considered optional.

The following examples are illustrative of the invention and its use. The electrolyzed saline solution used in Example X was obtained by subjecting about a 0.33% (about one third physiologically normal) saline solution to electrolysis for about 5 to 15 minutes. The voltage between the electrodes was maintained in the range of about 10 to 20 volts at a current in the range of about 5 to 20 amps. The freshly prepared electrolyzed saline when balanced or normalized with sterile 5% saline contained about 200 ppm of active chlorine species along with about 5 to 30 mg/L of ozone and corresponding amounts of molecular hydrogen and sodium and hydrogen ions. Precise measurements were not made.

Later solutions, i.e., all except in Example X, containing more precisely regulated amounts of ozone and active chlorine species were obtained using improved electrodes with closely controlled parameters of voltage, current, time and saline concentration. The following Example I delineates the preparation of a preferred electrolyzed saline for use in the present invention.

EXAMPLE I

To 300 ml of sterile distilled water was added 100 ml of sterile 0.9% saline resulting in a 0.225% saline solution. This solution was placed in a plastic chamber containing novel titanium and platinum electrodes. The 0.225% saline was then subjected to a current of 3 amperes at 20 volts (DC) for a period of three minutes. A 17 ml portion of this electrolyzed solution was aseptically diluted with 3 mls of a sterile 5% saline resulting in a finished isotonic electrolyzed saline having an active ozone content of 12±2 mg/L and an active chlorine species content of 60±4 ppm at a pH of 7.4. The chlorine concentration was determined using an Orion chlorine ion selective electrode and the ozone concentration was measured by a potassium indigo trisulfonate method according to the procedure of Hoigno et al. *Water Research*, 449–456 (1981).

EXAMPLE II

The stability of the solution prepared in. Example I was determined over a 24 hour period by making periodic ozone measurements as described by Hoigno et al. in Example I. The results are listed in Table I as follows:

TABLE I

| Time (hours) | Ozone Concentration (mg/L) |
|---|---|
| 0 | 12.35 ± 0.8 |
| 1 | 11.90 ± 0.7 |
| 2 | 12.64 ± 0.7 |
| 3 | 11.70 ± 0.8 |
| 21 | 11.78 ± 0.7 |
| 22 | 11.26 ± 0.7 |
| 23 | 11.67 ± 0.8 |

EXAMPLE III

The stability of electrolyzed solutions were further determined over an extended period of time at 4° C. Two separate isotonic solutions (Solution A and Solution B prepared using separate electrodes) were measured for stability. Each solution was electrolyzed and rendered isotonic using the same procedure as in Example I. The solutions were maintained at a temperature of 4° C. for a period of 200 hours and periodic measurements were made to determine active chlorine species ($Cl_2$) and ozone ($O_3$) contents. The results are shown in Table II as follows:

TABLE II

| Stability of $Cl_2$ and $O_3$ Over Time at 4° C. | | | | |
|---|---|---|---|---|
| | $Cl_2$ Concentration (ppm) | | $O_3$ Concentration (mg/Ml) | |
| Hours | A | B | A | B |
| 0 | 61.6 | 61.7 | 13.7 | 12.4 |
| 1 | 61.5 | 61.0 | 13.5 | 12.9 |
| 24 | 60.5 | 71.6 | 13.9 | 13.1 |
| 42 | 60.7 | NT* | 14.0 | NT* |
| 72 | 61.0 | 67.3 | 13.7 | 12.9 |
| 124 | NT* | 65.3 | NT* | 13.4 |

TABLE II-continued

Stability of $Cl_2$ and $O_3$ Over Time at 4° C.

| | $Cl_2$ Concentration (ppm) | | $O_3$ Concentration (mg/Ml) | |
|---|---|---|---|---|
| Hours | A | B | A | B |
| 176 | 60.8 | NT | 12.8 | NT* |
| 200 | 60.0 | 61.7 | 12.0 | 12.7 |

NT* = Not Tested

It is evident from the above that the solutions are stable in maintaining relatively constant the concentrations of the active chlorine species and ozone.

EXAMPLE IV

To show that the electrolysis reaction can be carried out effectively in saline solutions up to about 1% in concentration, the electrolysis reaction was carried out at saline concentrations of 0.3, 0.6 and 0.9% respectively. The active chlorine species ($Cl_2$) and ozone ($O_3$) contents were m&asured and are given in Table III as follows:

TABLE III $Cl_2$ and $O_3$ Content from Salines at Varying Concentrations

| Saline Concentration (% NaCl) | $Cl_2$ Concentration (ppm) | $O_3$ Concentration (mg/mL) |
|---|---|---|
| 0.3 | 129 | 21.8 |
| 0.6 | 161 | 26.6 |
| 0.9 | 168 | 28.0 |

As can be seen, the active ingredients are wall within the parameters required in the invention. The final active ingredient concentration can be adjusted by saline and/or water to provide a final active ingredient concentration as desired.

EXAMPLE V

The in vitro toxicity of the electrolyzed saline of Example I is illustrated by adding it to human lymphocytes at varying ozone and active chlorine agent concentrations and exposure intervals as shown in Table IV. Briefly, a 0.3% Trypan blue solution was prepared by combining 3 parts of a 1% Trypan blue solution (1 gram Trypan blue powder placed in a 100 ml volumetric flask and dissolved in water to a volume of 100 mls and then filtered prior to use) with 7 parts of RPMI 1640 media containing 10% FBS. A 1 mL sample of lymphocytes (e.g. $10^5$ live cells) was sedimented, the medium decanted, and the lymphocytes resuspended in an electrolyzed saline solution wherein the ozone and active chlorine species concentrations were modified by making selected dilutions with normalized saline. The lymphocytes were incubated for a selected time, then the lymphocytes were washed by sedimentation and resuspension in fresh medium. An aliquot of lymphocytes was then mixed with 0.3% Trypan blue solution and observed microscopically. One hundred cells were screened and the number of cells excluding Trypan blue was deemed as the percentage of viable cells.

TABLE IV

| Sample | Dilution of Electrolyzed Saline[a] | Exposure Period (min.) | Percent Viability[b] |
|---|---|---|---|
| A | 1:1 | 1.0 | 100 |
| B | 1:1 | 2.5 | 100 |
| C | 1:1 | 5.0 | 70 |
| D | 1:1 | 10.0 | 50 |
| E | 1:5 | 1.0 | 100 |
| F | 1:5 | 2.5 | 100 |
| G | 1:5 | 5.0 | 70 |
| H | 1:5 | 10.0 | 50 |
| I | 1:10 | 1.0 | 100 |
| J | 1:10 | 2.5 | 100 |
| K | 1:10 | 5.0 | 100 |
| L | 1:10 | 10.0 | 80 |
| M | 1:100 | 1.0 | 100 |
| N | 1:100 | 2.5 | 100 |
| O | 1:100 | 5.0 | 100 |
| P | 1:100 | 10.0 | 100 |
| Q | 1:1000 | 1.0 | 100 |
| R | 1:1000 | 2.5 | 100 |
| S | 1:1000 | 5.0 | 100 |
| T | 1:1000 | 10.0 | 100 |
| U[c] | 0 | 0 | 100 |
| V[d] | 0 | 0 | 100 |

[a] Parts electrolyzed saline contained in total parts saline solution, (1:1 = 100% electrolyzed saline of Example 1).
[b] Percent viability is a relative percentage with the percent viable versus the control adjusted to equal 100 percent.
[c] Titration control.
[d] Test control.

As documented in Table IV, 100% of cells exposed for 2.5 minutes to undiluted concentrations of electrolyzed saline were viable. At 5 and 10 minutes some toxicity to cells were noted at both 1:1 and 1:5 dilutions and at 1:10 minimal toxicity was noted at 10 minutes. For lesser times at the 1:10 dilution and at higher dilutions there was no toxicity noted up to 10 minutes.

EXAMPLE VI

The in vitro mutagenicity of the electrolyzed saline of Example I is illustrated by adding it to bacterial cells according to the Salmonella reverse mutation assay (Ames Test). This test was conducted by an independent testing laboratory in accordance with USFDA Good Laboratory Practices Regulations [21 C.F.R. Part 58].

The Ames tests employ several strains of *Salmonella typhimurium* which have been selected based on their sensitivity to mutation. The Ames tests were performed by mixing the electrolyzed saline of Example I with the test organism in a soft agar solution that contains only small amounts of histidine. The histidine permits the inoculated test organism to undergo a limited number of divisions, but is insufficient to permit normal growth. The tester strains require histidine for growth, due to a mutation in the gene that controls production of histidine. If, however, the strain undergoes a reverse mutation (spontaneous or induced by the test substance or a positive control material) the organism no longer requires histidine to grow and can produce a visible colony or revertant. Only mutations to the test organism in the region of the histidine gene will cause the test organism to undergo a reverse mutation to an organism that then no longer requires histidine. The tester strains were selected to detect various types of mutagens. The tester strains employed were TA97A, TA98, TA100, TA102, and TA1535.

The conclusion of the independent laboratory as to the mutagenicity of the electrolyzed saline solution is that the solution "tested against the five strains did not meet the criteria for a potential mutagen."

EXAMPLE VII

The in vivo toxicity of the electrolyzed saline of Example I is illustrated by injecting it into the tail vein of Harlan Sprague Dawley:ICR mice at varying concentrations, i.e. 2, 4, 6 and 8 mL/kg body weight. These tests were conducted by an independent testing laboratory in adherence with Good Laboratory Procedure regulations (21 C.F.R. Part 58). The conclusion of these tests was that "the electrolyzed saline solution of Example I was non-toxic at a single intravenous dose of at least 8 mL/kg b.w." The dose of 8 mL/kg b.w. is four times what was given to five human patients treated with electrolyzed saline solutions as will be described in Example XI.

EXAMPLE VIII

The in vitro activity of clinical isolates (field isolates) of HIV infected human lymphocytes was tested with the electrolyzed saline of Example I according to the method of Ho et al. *N. Eng. J. Med.* 321:1621–1625 (1989). The TCID (Tissue Culture Infectious Dose) per $10^6$ lymphocytes [PBMC (Peripheral Blood Mononuclear Cells)] was 5000 for each isolate. The p24 antigen was checked weekly for five weeks. The results at the end of five weeks are shown in Table V.

TABLE V

| Exposure Time (min) | Detectable p24 HIV Antigen | |
|---|---|---|
| | Isolate # 1 | Isolate # 2 |
| 1.0 | None | None |
| 2.5 | None | None |
| 5.0 | None | None |
| 10.0 | None | None |

As shown in Table V, there was a complete killing of HIV, as evidenced by the absence of detectable p24 antigen, after only one minute exposure. This provides evidence of the in vitro antiviral effectiveness of the electrolyzed saline in the treating of infected blood cells, whole blood, or any other fluid.

EXAMPLE IX

To further demonstrate the in vitro activity of the electrolyzed saline of Example I against HIV infected lymphocytes, additional testing was completed using the HIV infected laboratory isolate HB-2. The TCID (Tissue Culture Infectious Dose) ranged from $10^8$ to $10^1$ at an exposure time ranging from 1–10 minutes at dilutions of 1:1, 1:5 and 1:10. The results are given in Table VI.

TABLE VI

| ANTI-HIV ACTIVITY AGAINST HB-2 LABORATORY ISOLATE | | | | | | | | | |
|---|---|---|---|---|---|---|---|---|---|
| Dilut-ion | Expos-ure (min) | HB-2 Tissue Culture Infectious Dose (TCID) | | | | | | | |
| | | $10^8$ | $10^7$ | $10^6$ | $10^5$ | $10^4$ | $10^3$ | $10^2$ | $10^1$ |
| 1:1 | 1.0 | 0[a] | 0 | 0 | 0 | 0 | 0 | 0 | 0 |
| 1:1 | 2.5 | 0 | 0 | 0 | 0 | 0 | 0 | 0 | 0 |
| 1:5 | 1.0 | +[b] | + | 0 | 0 | 0 | 0 | 0 | 0 |
| 1:5 | 2.5 | + | + | 0 | 0 | 0 | 0 | 0 | 0 |

TABLE VI-continued

| ANTI-HIV ACTIVITY AGAINST HB-2 LABORATORY ISOLATE | | | | | | | | | |
|---|---|---|---|---|---|---|---|---|---|
| Dilut-ion | Expos-ure (min) | HB-2 Tissue Culture Infectious Dose (TCID) | | | | | | | |
| | | $10^8$ | $10^7$ | $10^6$ | $10^5$ | $10^4$ | $10^3$ | $10^2$ | $10^1$ |
| 1:5 | 5.0 | + | 0 | 0 | 0 | 0 | 0 | 0 | 0 |
| 1:5 | 10.0 | + | 0 | 0 | 0 | 0 | 0 | 0 | 0 |
| 1:10 | 1.0 | + | + | + | + | + | + | 8%[c] | 34% |
| 1:10 | 2.5 | + | + | + | + | + | + | 20% | 47% |
| 1:10 | 5.0 | + | + | + | + | + | + | 28% | 0 |
| 1:10 | 10 | + | + | + | + | + | + | d | 0 |

[a]No detection of p24 antigen in cultures after 5 weeks incubation.
[b]Greater than 380 pg/ml p24 antigen in cultures after 5 weeks incubation.
[c]Percent reduction of p24 antigen calculated as: sample well p24 antigen level divided by control well p24 antigen level minus 1 multiplied by 100.

It is evident from these results that, at an end point concentration of $10^8$ infected cells, complete killing occurred at a 1:1 dilution (full strength) after a one minute exposure. A 1:5 dilution of the saline was sufficient to kill a $10^7$ TCID of HIV after a 5 minute incubation period but not at 1 or 2 minute incubations. No killing of HIV occurred at a 1:10 dilution except at the lower $10^2$ and $10^1$ TCID concentrations.

As in Example VIII it is shown that the electrolyzed saline is effective in the in vitro killing of HIV in HB-2 isolates.

EXAMPLE X

This examples focuses on treatment of an AIDS patient in the last stages (i.e. WR6) of this disease. The patient was a male, age 53, who had tested positive several years earlier as being infected by the HIV virus. He had been hospitalized numerous times and had contracted pneumonia. He was extremely fatigued, had thrush in his mouth along with other usual AIDS related symptoms. This patient, realizing that his death was near, volunteered for treatment with electrolyzed saline containing 60±4 ppm of active chlorine species.

The patient was injected intravenously, first with 1.5 mg of colchicine followed by 30 cc of the balanced saline [26.25 cc of electrolyzed saline blended with 3.75 cc of 5% hypertonic saline] over a period of approximately 15 minutes followed about five minutes later by intravenous injection of 1000 mg of ascorbic acid. The patient was treated daily for five consecutive days with the same injections. There was no evidence of any abnormal side effects during the treatment period. The patient was monitored with continuous monitoring of a cardiogram. At the beginning of the first injection, the patient demonstrated a very irregular heart rhythm. At the end of the series of injections he showed marked improvement but still had a small amount of irregularity.

Subjectively, the patient stated that he felt better after each injection. His energy level increased daily and he was able to sleep better. The thrush in his mouth was improved. He was able to eat better and the pain associated with his disease was lessened.

Blood tests were conducted each day. There was no decrease in the red blood count and the blood showed no abnormalities or hemolysis. Repeat white blood counts revealed that the patient started with a leukocyte count of about 2000 with 10% lymphocytes. At the end of the fifth day the leukocyte count was 2625 with 20% lymphocytes. This means that the patient has a total lymphocyte count of 220 cells/mm³ at first and a total of 525 cells/mm³ at the end of five days.

EXAMPLE XI

As added evidence that the specification is enabling relative to the treatment of patients suffering from AIDS there follows a summary of testing of AIDS patients completed outside the United States.

Tests, using five (5) HIV positive male patients, were conducted in a foreign country under a protocol established and observed by the inventor and conducted under the supervision of licensed physicians in that country. The five patients, noted herein simply as AAA, BBB, CCC, DDD and EEE, were selected because they had been HIV positive for many years and had accepted AIDS syndrome as characterized by the history of having had opportunistic diseases. They were treated monthly for four series of treatments. Four of the patients were treated with a fifth series of treatments. Patient CCC terminated the test following the fourth series of treatment.

Each test was conducted for five days and repeated every fourth week throughout the series. Each patient received a daily intravenous dose of 1.0 mg of colchicine diluted in 20 cc of normal saline solution. Immediately following the colchicine there was administered, also intravenously, 120 cc of the isotonic electrolyzed saline solution containing 60±4 ppm chloride ion and about 12±2 mg/mL ozone. Ascorbic acid, 20,000 mg diluted in 45 cc of normal saline was intravenously administered with a minor amount being given between the colchicine and electrolyzed saline and the remainder following the electrolyzed saline administration. The four patients were followed with laboratorytests for an additional four months for a total of ten (10) months. The patients were not charged for the treatments and each signed a consent form for investigational study including the right to use and publish laboratory results. Each was informed that the treatment was experimental only and was not approved by the United States Food and Drug Administration.

Blood samples were drawn prior to the beginning of the test, on each day of the administration oft he solutions and at periodic intervals between the treatments and throughout the follow-up period subsequent to the treatments. The analysis of the blood samples was performed in the United States by major clinical laboratories. Complete laboratory test results were obtained. However, for purposes of this response, only the T4 cell absolute count is reported. As the AIDS disease progresses, there is typically a consistent decrease in the helper T4 cell count. It is accepted as a positive sign in the treatment of AIDS patients if an increase in the helper T4 lymphocytes can be demonstrated.

A summary of the T4 cell results are given in the following table.

TABLE VII

Absolute CD4 Counts Per Milliliter[a]

| Patient | Initial | 2 months | 6 months | 10 months | 24 months[b] |
|---------|---------|----------|----------|-----------|--------------|
| AAA | 79 | 132 (67%) | 177 (124%) | 192 (143%) | NA[c] |
| BBB | 949 | 1199 (26%) | 1042 (10%) | 1088 (15%) | 801 (−16%) |
| CCC | 198 | 344 (74%) | 278 (40%)[d] | NA | NA |
| DDD | 44 | 47 (7%) | 48 (9%) | 54 (23%) | NA |
| EEE | 278 | 391 (41%) | 355 (28%) | 355 (28%) | 297 (7%) |

[a]Counts represent an average of four determinations taken during each month for the interval described. The percentages in parentheses represent the percent of change from the initial counts.
[b]Patients did not receive electrolyzed saline therapy for one year after the ten month count was taken.
[c]Results not available.
[d]Five month average because CCC removed himself from the testing program.

The test results indicate that the T4 cell absolute count improved and stayed improved over the ten month follow up period in all four patients who completed their treatment. The T4 count in patient CCC also showed improvement during the period he was in the program.

While subjective in nature, Patient CCC, who discontinued his treatment, reported verbally that he continues to feel better and is working at his occupation. While also subjective in nature, the other patients reported they have felt improved health, have less fatigue, more energy, are able to work more, have less depression and possess a more positive attitude. Only minor side effects from the treatment were noted, i.e. some superficial phlebitis in the forearmwith discomfort due to the IV injections was noted and some gastrointestinal cramping was experienced.

It is quite clear from the above results that even those patients who did not show an immediate improvement following the first treatment, experienced a positive T4 cell count over the ten month period.

Other positive results were also noted in the study. Although consistent tests were not made, it was observed that there was an increase in the anti-p24 antibody titer. A decrease in anti-p24 antibody titer is generally seen with progression of the AIDS disease, therefore, any increase in anti-p24 antibody titer is an indication of an improvement resulting from the treatment. Late in the study, the p24 antigen corequantitative tests were negative in all four patients completing the testing, which is desirable. The HIV virus culture also showed "no virus isolated" for HIV growth in the four patients who completed the study. It is reported by the laboratory conducting the virus culture study, that it was able to recover the virus in 80–90% of the HIV positive patients tested and the culture is a sensitive test of infectiousness of the blood.

EXAMPLE XII

The in vivo toxicity of electrolyzed saline to the liver of a human patient is illustrated by normal levels of enzymes indicative of liver function in all five patients of Example XI. During the 10 month course of electrolyzed saline therapy, the only period for which data are available, the following enzyme levels were observed: aspartateaminotransferase (AST 1–45 U/L{SGOT}), alanine aminotransferase (ALT 1–35 U/L{SGPT}), and lactate dehydrogenase (LDH) 100–225 U/L.

EXAMPLE XIII

The stability of antibody to the p24 core antigen to detection by Western blot analysis remained positive during the course of electrolyzed saline therapy for patients AAA, BBB, DDD, and EEE. No data were available for patient CCC. This result is significant in that reports have documented that antibodies to the p24 antigen tend to become undetectable with the onset of clinical symptoms. J. Esteban et al., 2 Lancet 1083 (1985); J. Goudsmit et al., 155 J. Infect. Dis. 558 (1987).

EXAMPLE XIV

Increases in serum IgM levels for patients receiving electrolyzed saline therapy according to Example XI are illustrated in Table VIII. Four of the five patients showed an average increase in their serum IgM levels after four months of therapy, whereas one patient, CCC, displayed a 3% decrease. Normal ranges of serum IgM levels in adults are in the range of about 40–260 mg/L.

TABLE VIII

| Patient | Serum IgM Levels (mg/L) and % Change | |
|---|---|---|
| | Initial | 4 months |
| AAA | 96 | 330 (71%) |
| BBB | 318 | 364 (13%) |
| CCC | 151 | 147 (-3%) |
| DDD | 177 | 440 (60%) |
| EEE | 394 | 442 (11%) |

EXAMPLE XV

The stability of serum IgG levels of patients receiving electrolyzed saline therapy is illustrated in that all of the patients of Example. XI remained within the normal reference range of 700–1950 mg/dL.

EXAMPLE XVI

A male (FFF) who was HIV positive had an initial CD-4 count of 244 and a p24 antigen count of 114. This patient was treated with the solution of Example 1 for a series of 21 treatments over a one month period. No supplements such as moderating agents or colchicine were administered. The isotonio electrolyzed saline dosage was approximately 2 mg/kg body weight. Following treatments the energy level of the patient increased and the p24 antigen was negative. Follow up testing on FFF is continuing. After approximately 3.5 months from the date treatment was begun, his CD-4 count is 360 and his overall health continues to improve.

EXAMPLE XVII

A patient, MY, was enrolled in a NIH sponsored clinical trial for chronic, symptomatic patients with Hepatitis C infections. MV was treated with interferon and ribavirin for a six month period. Tests of liver function, including AST, ALT, and LDH continued to increase to levels exceeding 400 for AST and ALT and 700 for LDH. Because no clinical or laboratory improvement was seen by MV or attending physicians following the conclusion of the NIH clinical trial, MV elected to receive therapy using the electrolyzed saline of Example I. Following intravenous treatment at a dosage of 2 mg/kg body weight for five consecutive days a dramatic drop in the AST, ALT and LDH levels were observed. One month after receiving the electrolyzed saline therapy, ALT, AST and LDH values were reestablished within normal ranges and the overall health of MV was stated to being comparable to before becoming symptomatic for Hepatitis C. MV continues to demonstrate good health and laboratory findings show measured parameters to be within normal ranges.

The above examples show there is evidence that the in vitro and in vivo use of electrolyzed saline in treating physiological solutions and patients in accordance with the invention resulted in decontamination of solutions and marked improvement in patients with no visible toxic side effects.

I claim:

1. A microbiocidal solution for in vitro treatment of a microbially contaminated fluid selected from the group consisting of whole blood, blood cells, blood plasma, and mixtures thereof and for treatment of microbial infections in warm blooded animals comprising a sterile electrolyzed saline containing ozone and active chlorine species wherein the ozone content is in the range of about 5–100 mg/L and the active chlorine species content is in the range of about 5–300 ppm.

2. A microbiocidal solution according to claim 1 which has an isotonic saline concentration.

3. A microbiocidal solution according to claim 1 wherein the ozone content is in the range of about 5–30 mg/L and the active chlorine species content is in the range of about 10–100 ppm.

4. A microbiocidal solution according to claim 3 which has an isotonic saline concentration.

5. A microbiocidal solution according to claim 1 wherein the ozone content is in the range of about 9–15 mg/L and the active chlorine species content is in the range of about 10–80 ppm.

6. A microbiocidal solution according to claim 5 which has an isotonic saline concentration.

* * * * *